(12) United States Patent
Sakaki (10) Patent No.: US 10,973,247 B2
(45) Date of Patent: Apr. 13, 2021

(54) FOOD TASTE REPRODUCTION SYSTEM, FOOD TASTE REPRODUCTION DATA CONVERSION APPARATUS, AND FOOD TASTE REPRODUCTION METHOD

(71) Applicant: DENTSU INC., Tokyo (JP)

(72) Inventor: Ryosuke Sakaki, Tokyo (JP)

(73) Assignee: DENTSU INC., Tokyo (JP)

(*) Notice: Subject to any disclaimer, the term of this patent is extended or adjusted under 35 U.S.C. 154(b) by 327 days.

(21) Appl. No.: 16/085,286

(22) PCT Filed: Mar. 16, 2017

(86) PCT No.: PCT/JP2017/010562
§ 371 (c)(1),
(2) Date: Sep. 14, 2018

(87) PCT Pub. No.: WO2017/159765
PCT Pub. Date: Sep. 21, 2017

(65) Prior Publication Data
US 2019/0082722 A1 Mar. 21, 2019

(30) Foreign Application Priority Data

Mar. 17, 2016 (JP) .............................. JP2016-053311

(51) Int. Cl.
*A23L 5/00* (2016.01)
*G01N 33/02* (2006.01)
(Continued)

(52) U.S. Cl.
CPC ................. *A23L 5/00* (2016.08); *A23P 30/00* (2016.08); *A23P 30/10* (2016.08); *A47J 43/00* (2013.01);
(Continued)

(58) Field of Classification Search
CPC ...... A23L 5/00; G06T 7/50; G06T 7/90; A47J 43/20; A47J 43/00; A23P 30/00;
(Continued)

(56) References Cited

U.S. PATENT DOCUMENTS

| 5,482,855 A | 1/1996 | Yamafuji et al. |
| 6,503,701 B1 * | 1/2003 | Bauer ................... B82Y 15/00 |
| | | 435/283.1 |

(Continued)

FOREIGN PATENT DOCUMENTS

| CN | 105196553 A | 12/2015 |
| CN | 204949484 U | 1/2016 |

(Continued)

OTHER PUBLICATIONS

Hidemitsu Furukawa, "3D-designable-gels Acceleration of Japanese-style Makers Revolution", Journal of the Society of Rubber Industry, vol. 87, No. 9, 2014, pp. 389-394, together with an English-language abstract.

(Continued)

*Primary Examiner* — Shogo Sasaki
(74) *Attorney, Agent, or Firm* — Greenblum & Bernstein, P.L.C.

(57) ABSTRACT

In a food taste reproduction system, a taste recognition device obtains the taste data obtained by quantifying the food taste. A first terminal converts the taste data into taste reproduction data on a component ratio of taste components for reproducing the food taste by combining a plurality of the taste components, the taste component containing a material providing at least one basic taste. The first terminal transmits the taste reproduction data to the server for storing. A second terminal receives the taste reproduction data via an Internet and outputs the taste reproduction data to a taste reproduction device. The taste reproduction device selects at (Continued)

least two taste components among a plurality of the taste components based on the taste reproduction data, and combines the selected taste components in accordance with the component ratio so as to obtain the taste reproduced material.

13 Claims, 7 Drawing Sheets

(51) Int. Cl.
| | |
|---|---|
| B33Y 50/00 | (2015.01) |
| A23P 30/00 | (2016.01) |
| A47J 43/00 | (2006.01) |
| B29C 67/00 | (2017.01) |
| A23P 30/10 | (2016.01) |
| G06T 7/50 | (2017.01) |
| G06T 7/90 | (2017.01) |
| A47J 43/20 | (2006.01) |
| A23P 20/25 | (2016.01) |

(52) U.S. Cl.
CPC ............... *A47J 43/20* (2013.01); *B29C 67/00* (2013.01); *B33Y 50/00* (2014.12); *G01N 33/02* (2013.01); *G06T 7/50* (2017.01); *G06T 7/90* (2017.01); *A23P 2020/253* (2016.08); *A23V 2200/15* (2013.01); *A23V 2200/16* (2013.01)

(58) Field of Classification Search
CPC ............... A23P 30/10; A23P 2020/253; A23V 2200/15; A23V 2200/16; G01N 33/02; B29C 67/00; B33Y 50/00
See application file for complete search history.

(56) References Cited

U.S. PATENT DOCUMENTS

| | | | | |
|---|---|---|---|---|
| 7,785,889 B2* | 8/2010 | Kaneda | ................. | G01N 33/68 436/24 |
| 7,858,036 B2* | 12/2010 | Kugimiya | ............ | G01N 27/327 422/68.1 |
| 10,702,695 B2* | 7/2020 | Costanzo | ............... | G16H 20/10 |
| 2013/0228016 A1 | 9/2013 | Sakurai et al. | | |
| 2013/0309373 A1 | 11/2013 | Tan et al. | | |
| 2016/0135493 A1 | 5/2016 | Kuo et al. | | |
| 2016/0165935 A1 | 6/2016 | Eddy et al. | | |

FOREIGN PATENT DOCUMENTS

| | | |
|---|---|---|
| CN | 105394801 A | 3/2016 |
| JP | 2578370 B2 | 11/1996 |
| JP | H09-187232 A | 7/1997 |
| JP | 2002-077444 A | 3/2002 |
| JP | 4574828 B2 | 8/2010 |
| JP | 2013-544596 A | 12/2013 |
| JP | 2014-50336 A | 3/2014 |
| JP | 2016-116497 A | 6/2016 |
| WO | 2012/029888 A1 | 3/2012 |
| WO | 2012/073171 A1 | 6/2012 |
| WO | 2013/108912 A1 | 7/2013 |
| WO | 2014/009280 A2 | 1/2014 |
| WO | 2014/190168 A1 | 11/2014 |
| WO | 2014/190217 A1 | 11/2014 |
| WO | 2015/006812 A1 | 1/2015 |

OTHER PUBLICATIONS

International Search Report issued in International Bureau of WIPO Patent Application No. PCT/JP2017/010562, dated Jun. 20, 2017, together with an English translation thereof.
Kiyoshi Toko et al., "Review Article; A taste sensor", Measurement Science and Technology, IOP, Bristol, GB, vol. 9, No. 12, XP020064666, Dec. 1, 1998, pp. 1919-1936.
Search Report issued in European Patent Office (EPO) Patent Application No. 17766761.5, dated Sep. 16, 2019.

* cited by examiner

FOOD TASTE REPRODUCTION SYSTEM, FOOD TASTE REPRODUCTION DATA CONVERSION APPARATUS, AND FOOD TASTE REPRODUCTION METHOD

TECHNICAL FIELD

The present invention relates to a food taste reproduction system, a food taste reproduction data conversion apparatus, and a food taste reproduction method.

BACKGROUND ART

It has been developed a taste sensor that detects not ingredients of a food but tastes to be sensed by a human tongue and outputs as an electrical signal. Especially, a taste sensor configured to detect basic tastes of a saltiness, an acidity, a bitterness, a sweetness, and an umami taste has been developed (for example, see Patent Document 1).

Patent Document 1 discloses a lipid membrane sensor electrode where a lipid membrane and an electrode are disposed on a base material, and a large number of the lipid membrane sensor electrodes using lipid membranes with different response characteristics are arranged in parallel to constitute a taste sensor array. Into a solution to be measured, a reference electrode as an electrode that generates an electric potential as a reference of the measurement is put with the taste sensor array. An electrical signal from the lipid membrane is amplified by an amplifier and applied to an A/D converter. An electrical signal from the reference electrode is also applied to the A/D converter, and an electric potential difference between the lipid membrane and the reference electrode is converted into a digital signal. This digital signal is appropriately processed by a microcomputer to be indicated on an X-Y recorder.

As an application of the taste sensor disclosed in, for example, Patent Document 1, there has been a proposal to apply to, for example, a taste test on a food and a medicinal product (for example, see Patent Document 2). Use of the taste sensor in the taste test has solved a problem that: in a sensory test on a food, for example, individual differences among panelists and a physical condition of a panelist causes a variation to prevent precisely obtaining a subtle difference in strength even on an identical taste, thus failing to perform a test with a high reproducibility: or in a case where a test target is a medicinal product, a usable amount for the test is limited for a health of the panelist, thus failing to perform an efficient test.

Patent Document 1: Japanese Patent No. 2578370
Patent Document 2: Japanese Patent No. 4574828

DISCLOSURE OF THE INVENTION

Problems to be Solved by the Invention

Use of the taste sensor ensures detecting the taste to be sensed by a human tongue and outputting the taste as the electrical signal to convert into data. For example, the taste sensor can be used to convert a taste of a dish cooked by a famous chef into data to visualize the taste.

However, for the reproduction of the taste of the dish cooked by the famous chef, it is necessary to prepare not the taste data but foodstuffs and seasonings, and cook as well as the famous chef by referring to a recipe of the famous chef. The taste data can be used to evaluate a degree of the reproduction, while it is hard to say that the taste data is effectively used.

The present invention has been made based on the above-described problem, and it is one of objects of the present invention to provide a food taste reproduction system configured to easily reproduce a food taste based on taste data, a food taste reproduction data conversion apparatus, and a food taste reproduction method.

Solutions to the Problems

According to a first aspect of the present invention, a food taste reproduction system includes a first computer and a taste reproduction device. The first computer converts taste data into taste reproduction data. The taste data is obtained by quantifying a taste of a food. The taste reproduction data is data on a component ratio of taste components for reproducing the taste by combining a plurality of the taste components. The taste component contains a material providing at least one basic taste. The taste reproduction device obtains a taste reproduced material such that the taste reproduction device selects at least two taste components among the plurality of the taste components based on the taste reproduction data and combines the selected taste components according to the component ratio.

This configuration converts the taste data into the taste reproduction data on the component ratio of the taste components such that at least two taste components among the plurality of the taste components are selected based on the taste reproduction data and the selected taste components are combined according to the component ratio, and then, the taste reproduced material can be obtained.

In the food taste reproduction system of the first aspect of the present invention, preferably, the taste reproduction device further includes a shaping device that shapes the taste reproduced material into a shape of the food based on shape data on the shape of the food.

In the food taste reproduction system of the first aspect of the present invention, preferably, the shaping device mixes a food base material with the taste component based on texture data on a texture of the food, and adds the texture of the food to the taste reproduced material.

In the food taste reproduction system of the first aspect of the present invention, preferably, the taste reproduction device further includes a coloring device that performs coloring on the taste reproduced material based on color data of the food.

In the food taste reproduction system of the first aspect of the present invention, preferably, the first computer refers to eating person data on an eating person who eats the taste reproduced material to select the taste component or decide an amount of the taste component corresponding to the eating person.

Preferably, the food taste reproduction system of the first aspect of the present invention further includes a taste sensor that outputs the taste as an electrical signal, and a second computer that outputs the taste data obtained by quantifying the taste based on the electrical signal output by the taste sensor.

In the food taste reproduction system of the first aspect of the present invention, preferably, the taste reproduction device includes a plurality of storage containers, a supply unit, and a combination unit. The plurality of the storage containers separately store a plurality of the taste components. The supply unit supplies any amount of the taste components from at least two of the plurality of the storage containers based on the taste reproduction data. The combination unit combines the plurality of taste components supplied from the supply unit.

According to another aspect of the present invention, a food taste reproduction data conversion apparatus includes a processor and at least one external interface. The processor receives taste data via the external interface. The taste data is obtained by quantifying a taste of a food based on an electrical signal. The electrical signal is output by a taste sensor. The taste sensor outputs the taste of the food as the electrical signal. And the processor converts the taste data into taste reproduction data. The taste reproduction data is data on a component ratio of taste components for reproducing the taste of the food by combining a plurality of the taste components. The taste component contains a material providing at least one basic taste. The processor transmits the taste reproduction data via the external interface.

According to another aspect of the present invention, a food taste reproduction method includes a step of converting taste data into taste reproduction data with a first computer, the taste data being obtained by quantifying a taste of a food, the taste reproduction data being data on a component ratio of taste components for reproducing the taste of the food by combining a plurality of the taste components, the taste component containing a material providing at least one basic taste, and a step of obtaining a taste reproduced material such that a second computer controls a taste reproduction device that selects at least two taste components among a plurality of the taste components based on the taste reproduction data and combines the selected taste components according to the component ratio.

Effects of the Invention

With the present invention, taste data is converted into taste reproduction data on a component ratio of taste components such that at least two taste components among a plurality of the taste components are selected based on the taste reproduction data and the selected taste components are combined according to the component ratio, and then, the taste reproduced material can be obtained. Accordingly, the taste of the food can be easily reproduced based on the taste data.

DESCRIPTION OF PREFERRED EMBODIMENTS

The following describes a food taste reproduction system according to the embodiment.

<Outline>

The food taste reproduction system according to the embodiment includes a first computer and a taste reproduction device. The first computer converts taste data into taste reproduction data. The taste data is obtained by quantifying a taste of a food. The taste reproduction data is data on a component ratio of taste components for reproducing the taste by combining a plurality of the taste components. The taste component contains a material providing at least one basic taste. The taste reproduction device obtains a taste reproduced material such that the taste reproduction device selects at least two taste components among the plurality of the taste components based on the taste reproduction data and combines the selected taste components according to the component ratio.

Here, the food is a product to be ingested by a human. For example, the food includes food materials before processing, preparation, and cooking; a processed food provided by processing, preparing, or cooking at least one food material; a prepared food and a dish: a medicinal product; and a supplement.

A state of the food is not limited in particular, and may be any of, for example, a food in a solid state, a tablet, a powder, a granule, a liquid beverage, and a gel (a jelly).

The taste data is data obtained by quantifying a taste to be sensed by a tongue, and not ingredient data of the taste. The taste data is, for example, data obtained by quantifying strength of the taste for each basic taste.

The basic taste includes, for example, the five tastes that can be sensed by the human tongue: an acidity, a bitterness, a sweetness, a saltiness, an umami taste, and a pungency and an astringency, which are tastes stimulating a sense of pain, may be added. Furthermore, the taste can be distinguished into "first taste" felt immediately after taking food in one's mouth and "aftertaste" felt later and remaining for a while. "First taste" includes "acidity," "bitterness odd taste," "astringency stimulus," "umami taste," "saltiness," and "sweetness", and "aftertaste" includes "mineral-based bitterness," "bitterness for food," "astringency," and "umami fullness."

These tastes are merely exemplary basic tastes, and it can be conveniently set how many basic tastes the taste of the food is divided into. It can be conveniently set which basic taste is used for the taste data.

The taste data can be measured from a food specimen using, for example, a taste recognition device that includes a taste sensor.

The taste recognition device includes the taste sensor that outputs the food taste as an electrical signal, and a second computer that outputs the taste data obtained by quantifying the food taste based on the electrical signal output by the taste sensor.

Here, the taste sensor is a device that outputs a taste to be sensed by a human tongue as an electrical signal. The taste sensor is, for example, the taste sensor using the lipid membrane disclosed in Patent Document 1. However, the taste sensor is not specifically limited.

When the taste sensor disclosed in Patent Document 1 is used, the taste recognition device includes, for example, a container into which a solution to be measured is put, a reference electrode, the taste sensor, a voltage detector that detects a membrane potential of the taste sensor based on an electric potential of the reference electrode, an A/D converter that converts the output by the voltage detector into a digital value, the second computer that performs a process such as an operation on the output by the A/D converter, and an output device (a printer, a display, and the like) that outputs a result of the process by the second computer.

The taste recognition device that includes the taste sensor using the lipid membrane is commercially available, for example, a taste recognition device TS-5000Z manufactured by Intelligent Sensor Technology, Inc., while the taste recognition device is not specifically limited.

In the food taste reproduction system according to the embodiment, the first computer as a food taste reproduction data conversion apparatus converts the taste data obtained by quantifying the food taste into the taste reproduction data on a component ratio of taste components for reproducing the food taste by combining a plurality of the taste components, the taste component including a material providing at least one basic taste.

Here, the taste component is a component that is used for reproducing the food taste and includes a material providing at least one basic taste. The taste component is not a material of an original food.

For example, the taste component is a foodstuff itself (milk, barley tea, and the like), an extract of the foodstuff (a coffee extract and the like), a seasoning (sugar, salt, and the like), or a chemical substance (hydrochloric acid, citric acid, tartaric acid, caffeine, and the like).

One taste component may provide a plurality of basic tastes. For example, though the barley tea provides the bitterness, the fullness, and the umami taste as the basic taste, the barley tea is usable as the taste component.

The taste reproduction data is information including types and the component ratios of at least two taste components.

In the food taste reproduction system according to the embodiment, the taste reproduction device selects at least two taste components among the plurality of taste components based on the taste reproduction data output from the first computer, and combines the selected taste components according to the component ratio, thus obtaining a taste reproduced material.

Here, the taste reproduced material is a material having a taste identical or similar to the taste of the original food. It is not necessary for the taste reproduced material to include the foodstuffs identical to the foodstuffs of the original food, and it is only necessary that the eaten material provides a taste equal to that of the original food.

A state of the taste reproduced material is not specifically limited. The state of the taste reproduced material may be any of solid, liquid, gas, and colloid (including gel and sol), and may be a combination.

The taste reproduction device combines a plurality of the taste components based on the taste reproduction data, thus reproducing the taste of the original food.

Here, the combination includes, for example, the combination (combine), mixture (mix), and blending (blend).

The taste reproduction device includes, for example, a plurality of storage containers that separately store the plurality of the taste components, a supply unit that supplies at least two taste components by any amount among the plurality of the storage containers based on the taste reproduction data, and a combination unit where the plurality of taste components supplied from the supply unit are combined.

The combination unit includes, for example, dispensers that discharge the plurality of the taste components from the storage containers into one container, a blender that blends the plurality of the taste components, a mixer that mixes the plurality of the taste components, and shaping equipment that shapes the plurality of the taste components into one object.

Preferably, the taste reproduction device further includes a shaping device that shapes the taste reproduced material into a shape of the food based on shape data on a shape of the food.

Here, the shape data is data obtained by, for example, reading the shape of the food with a 3D scanner and quantifying the shape.

The 3D scanner is a device that senses an unevenness of the object to retrieve the unevenness as 3D data. The 3D scanner obtains a plurality of pieces of three-dimensional coordinate data (X, Y, Z) while irradiating the object with a laser and applying a pressure-sensitive sensor, and outputs point cloud data.

One concrete example of the shaping equipment is a 3D printer. The 3D printer is a shaping device that laminates and solidifies a material little by little to make a three-dimensional object as designed. A shaping method includes, mainly, a powder sintering, a hot-melt extrusion, a stereolithography, an inkjet, and similar method.

In the embodiment, the shaping with the 3D printer includes a case where the taste components are shaped into one object after mixing, a case where the taste components are shaped into one object without mixing, and a case where they are combined.

The 3D data used for shaping by the 3D printer may be point source data output from the 3D scanner, and the point source data may be converted into data in a surface format to be used as, for example, polygon data. Thus, the format of the 3D data is not specifically limited.

Preferably, the shaping device mixes a food base material with the taste component based on texture data on a texture of the food, and adds the texture to the taste reproduced material.

Here, the texture means a skin sensation inside an oral cavity including teeth and a tongue among the five senses sensed in having a food. Specifically, the texture includes, for example, a chewiness, a touch on the tongue, and a smoothness to the throat.

The texture data is, for example, information output from a texture measurement device. The texture measurement device uses a pressure sensor and the like to quantify the texture of the food. More specifically, for example, on elasticity, the texture measurement device presses a conical-shaped probe onto the food to measure its stress with a pressure sensor. On hardness, the texture measurement device cuts the food with a wedge-shaped probe to measure with its stress sensor.

The food base material is a material for adding a desired state to the food. The food base material may be tasteless and odorless, or have a taste and a smell, thus being not specifically limited.

One of the most preferable food base materials is a gel (a jelly). The gel is neither a solid nor a liquid, but a network structure of molecules including a solvent to be bulged. The gel varies from a liquid having a soft viscosity to a hard solid due to its chemical composition and various factors.

The gel is a material obtained by solidifying a liquid with a gelatinizing agent. The gelatinizing agent includes a chemical gel cross-linked by a chemical bond and a physical gel cross-linked by a physical association. For example, agar, gelatin, and pectin as natural foodstuffs are the physical gels.

A description will be given of a case where the taste reproduced material is formed using, for example, the inkjet method for the 3D printer and the physical gel for the food base material, respectively. First, the gelatinizing agent is added to water and dispersed, and additionally, the taste component is dissolved or dispersed into a liquid. The mixture is warmed to a temperature higher than a solidification temperature in hot water and slowly stirred so as not to harden, thus the taste is uniformed. Then, water with a coagulant, which has been warmed and stirred, is added little by little and mixed. The consequently obtained mixture is output from a thin nozzle to form the shape based on the 3D data. Since the mixture is in the soft gel state at the output moment, a cooling gas is applied to instantaneously solidify the mixture. Consequently, the taste reproduced material is obtained.

Selecting the type and the amount of the gelatinizing agent allows the hardness and the elasticity to be changed, thus ensuring easy reproduction of the texture of the original food. It is ensured to vary the temperature of the gel to adjust the taste.

Preferably, the taste reproduction device further includes a coloring device that performs coloring on the taste reproduced material based on color data of the food.

The coloring device is, for example, an inkjet printer, and is configured to select an edible ink based on the color data to spray the edible ink to the taste reproduced material, while the coloring device is not specifically limited.

The color data is information output from a color scanner that detects the color of the food. For example, a color filter or the like is used to perform a color separation of a reflected light of a laser, with which the above-described 3D scanner irradiates the object, into RGB, and an image sensor (CCD and the like) can sense the respective colors of the RGB, output the electrical signal, and perform the A/D conversion on these to output as the color data. Note that, the color scanner may be provided separately from the 3D scanner.

The taste component contains nutrients such as protein, lipid, carbohydrate, mineral, and vitamin, a salt content, a sugar content, an alcohol content, and similar content in some cases. When someone has the nutrient to be ingested and when he/she has an ingestion restriction of the salt content and the sugar content depending on, for example, an activity status, a physical condition, and a symptom, it is preferred that, in selecting the taste component, the taste component containing large amounts of this nutrient is selected, or the taste component containing the salt content or the sugar content is excluded from options.

Therefore, in the food taste reproduction system according to the embodiment, preferably, the first computer refers to eating person data on an eating person who eats the taste reproduced material to select the taste component and decide the amount of the taste component corresponding to the eating person.

The eating person data includes both information directly pertaining the selection and the amount of the taste component, for example, the type and the amount of the nutrient to be ingested by the eating person and ingestion upper limits of the salt content and the sugar content, and indirect information referred in determining the selection and the amount of the taste component, for example, an age, a gender, an activity status, an activity plan, a physical condition, a symptom, and a result of a physiologic inspection of the eating person.

The eating person data may include information on an environment where the eating person eats the taste reproduced material. For example, since a taste change due to the environment occurs, for example, the saltiness becomes hard to be felt in space, preferably, the conversion into the taste reproduction data is performed considering the change.

Next, a description will be given of a relationship between the first computer and the taste reproduction device in the food taste reproduction system according to the embodiment.

The first computer may output the taste reproduction data converted from the taste data to the taste reproduction device, or may store the taste reproduction data in a storage unit.

When the first computer outputs the taste reproduction data to the taste reproduction device, for example, the taste reproduction device may be coupled to the first computer with a communication cable such as a serial cable, and the taste reproduction data is transferred through a data transfer communication between information equipment.

Meanwhile, when the first computer stores the taste reproduction data in the storage unit, the first computer may output the taste reproduction data to a coupled storage device and store the taste reproduction data. In this case, the first computer reads the taste reproduction data stored in the storage device corresponding to a request from the taste reproduction device, and transmits the taste reproduction data to the taste reproduction device.

The first computer itself may be a server coupled to a network such as the Internet or a LAN. In this case, the server reads the taste reproduction data stored in the storage device corresponding to the request from the taste reproduction device, and transmits the taste reproduction data to the taste reproduction device.

The first computer may transmit the taste reproduction data to an additionally disposed server for storage. In this case, the server reads the taste reproduction data stored in the storage device corresponding to the request from the taste reproduction device, and transmits the taste reproduction data to the taste reproduction device.

In these cases, the taste reproduction data may be requested from not the taste reproduction device but a third computer, which is configured to be coupled to the taste reproduction device, to the first computer or the server, and the third computer may once receive the taste reproduction data to output to the taste reproduction device. In this case, as an example of the output of the taste reproduction data, the taste reproduction device may be coupled to the third computer with a communication cable such as a serial cable or through a wireless communication such as Bluetooth (registered trademark) or WiFi, and the taste reproduction data is transferred through the data transfer communication between the information equipment.

For example, the first computer may cause a coupled memory card writer to store the taste reproduction data in a memory card. In this case, a memory card reader is coupled to the taste reproduction device or the third computer, and the taste reproduction data is read from the memory card.

The first computer may transmit the taste reproduction data to the third computer coupled by, for example, Bluetooth or WiFi and cause a memory or a storage device of the third computer to store the taste reproduction data, thus outputting the taste reproduction data from the third computer to the taste reproduction device.

Furthermore, the first computer may convert the taste reproduction data into a barcode, output on a medium such as paper, take a picture of this barcode with a camera included in the third computer, recognize the barcode, and convert into the taste reproduction data, and the third computer outputs the taste reproduction data to the taste reproduction device.

As described above, there is various means for passing the taste reproduction data from the first computer to the taste reproduction device, and the means is not limited to any one.

Next, a description will be given of a relationship between the first computer and the second computer that constitutes the taste recognition device.

When the second computer outputs the taste data to the first computer, for example, the first computer may be coupled to the second computer with a communication cable such as a serial cable, and the taste data is transferred through the data transfer communication between the information equipment. The first computer may be coupled to the second computer through a network, and the taste data is transferred to the first computer via the network. A plurality of the second computers mar be coupled to the first computer.

The second computer may be coupled to a computer other than the first computer with a communication cable, and the other computer is coupled to the first computer via a network. In this case, the taste data is transferred from the second computer to the other computer via the communication cable, and the other computer transmits the taste data to the first computer via the network.

The first computer may double as the second computer. That is, one computer may ensure both functions of the first computer and the second computer. The first computer may be read differently as a first processor and the second computer may be read differently as a second processor such that two processors are driven in one computer to ensure mutually different functions.

As one embodiment of the present invention, there is a case where the first computer doubles as the second computer, and the first computer causes the server disposed on the network such as the Internet to store the taste reproduction data. In this case, the third computer configured to be coupled to the taste reproduction device may be additionally disposed such that the third computer obtains the taste reproduction data from the server and outputs to the taste reproduction device.

With the above-described food taste reproduction system according to the embodiment, the first computer converts the taste data obtained by quantifying the food taste into the taste reproduction data on the component ratio of the taste components for reproducing the food taste by combining the plurality of the taste components. Then, the taste reproduction device selects at least two taste components among the plurality of the taste components based on the taste reproduction data, and combines the selected taste components according to the component ratio included in the taste reproduction data, thus obtaining the taste reproduced material.

Figure 1:
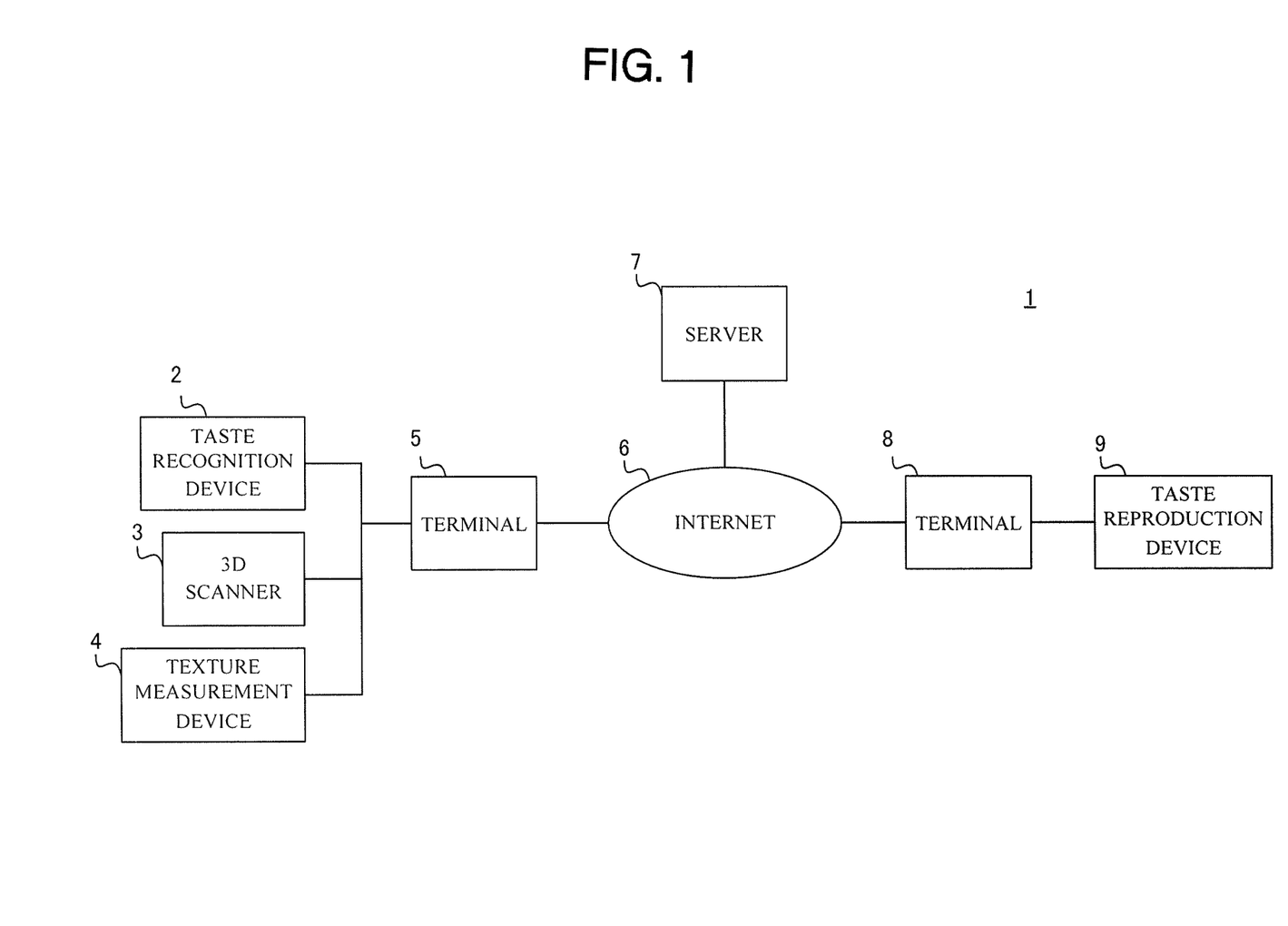
FIG. 1 is a schematic diagram illustrating a food taste reproduction system according to an embodiment of the present invention.

The following describes the food taste reproduction system according to the embodiment of the present invention in detail by referring to attached drawings. The food taste reproduction system, the food taste reproduction data conversion apparatus, and the food taste reproduction method according to the present invention are not limited to the following embodiments, and can be performed in various modifications in a range of the gist of the present invention.
<System>
FIG. 1 is a schematic diagram illustrating the food taste reproduction system according to the embodiment of the present invention. A food taste reproduction system 1 according to the embodiment includes a taste recognition device 2, a 3D scanner 3, a texture measurement device 4, a first terminal 5, Internet 6, a server 7, a second terminal 8, and a taste reproduction device 9.

Figure 2:
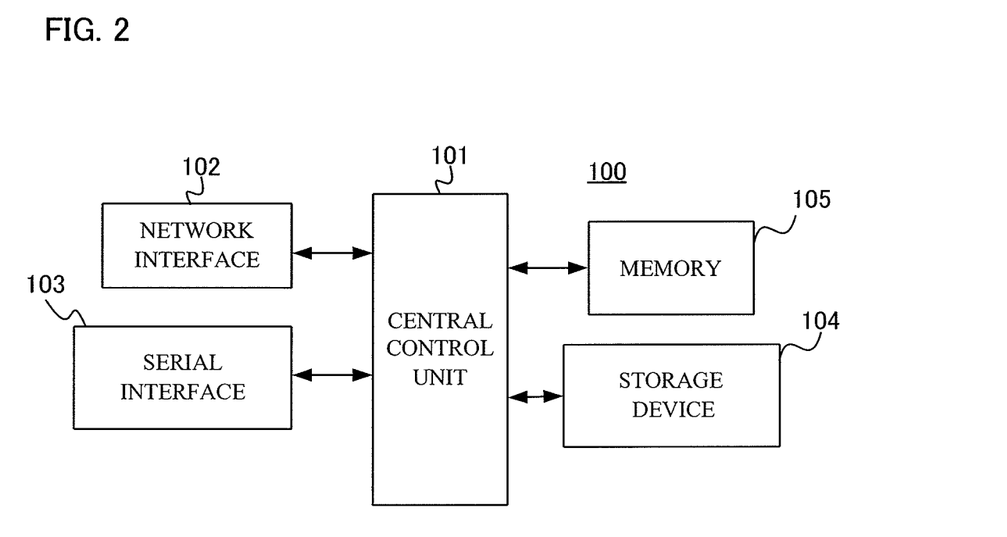
FIG. 2 is a block diagram illustrating hardware of a computer in the food taste reproduction system according to the embodiment of the present invention.

Here, for easy explanation, one taste recognition device 2, one 3D scanner 3, one first terminal 5, one second terminal 8, and one taste reproduction device 9 are illustrated, while a large numbers of the respective units may be disposed.
<Computer>
FIG. 2 is a block diagram illustrating hardware of the computer in the food taste reproduction system according to the embodiment of the present invention.

As illustrated in FIG. 2, a computer 100 includes a central control unit 101, a network interface 102, a serial interface 103, a storage device 104, and a memory 105.

The central control unit 101 controls each unit of the computer 100. Specifically, the central control unit 101 includes, for example, a Central Processing Unit (CPU), and uses the memory 105 to perform various control operations according to an OS and various processing programs.

The network interface 102 as an exemplary external interface executes data communication and the like via, for example, the Internet 6.

The serial interface 103 as an exemplary external interface executes a data communication and the like with an external device, for example, according to a serial bus standard such as a Universal Serial Bus (USB) via the communication cable and the like. Instead of the serial interface 103, a parallel interface may be used.

The storage device 104 as a storage unit includes, for example, a non-volatile memory, and stores various programs and data necessary for the operations of the central control unit 101.

The memory 105 as a storage unit includes, for example, a Dynamic Random Access Memory (DRAM), and functions as a buffer memory temporarily stores, for example, data processed by the central control unit 101 and the like and a working memory for the central control unit 101 and the like.

Figure 3:
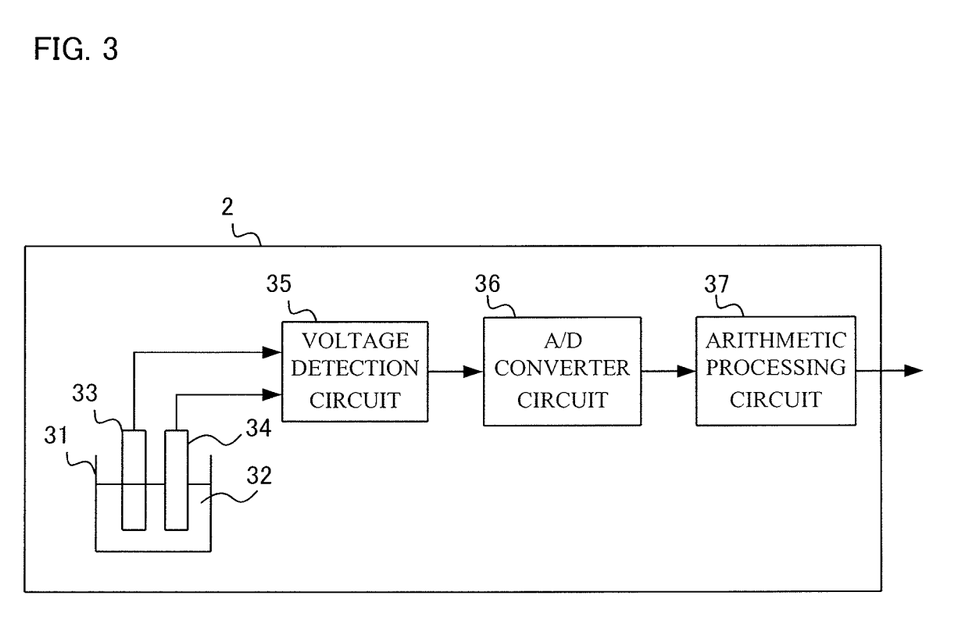
FIG. 3 is a block diagram illustrating a taste recognition device in the food taste reproduction system according to the embodiment.

In the above-described computer 100, the programs and the data appropriately prepared corresponding to objects can realize the first terminal 5, the server 7 and the second terminal 8.
<Taste Recognition Device>
FIG. 3 is a block diagram illustrating the taste recognition device in the food taste reproduction system according to the embodiment. As illustrated in FIG. 3, the taste recognition device 2 includes a container 31 into which a solution to be measured 32 is put, a taste sensor 33, a reference electrode 34, a voltage detection circuit 35, an A/D converter circuit 36, and an arithmetic processing circuit 37.

While the taste sensor 33 is the taste sensor using the lipid membrane disclosed in Patent Document 1, the taste sensor 33 is not specifically limited.

Figure 4:
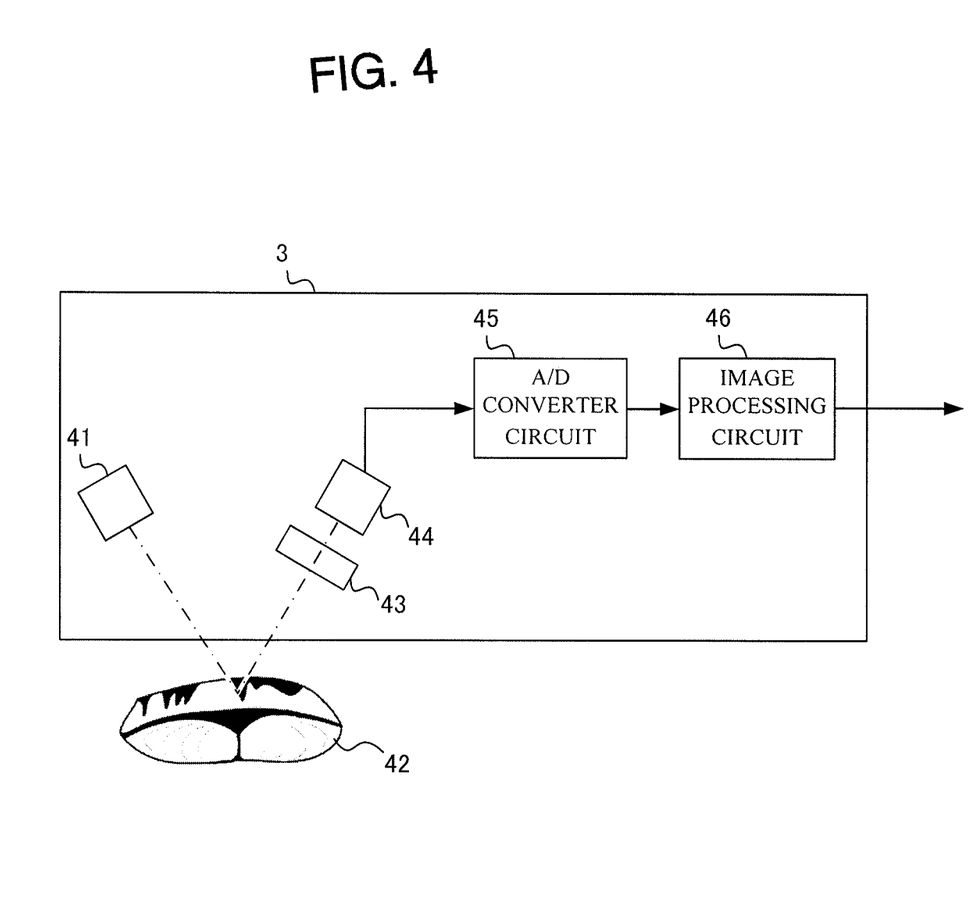
FIG. 4 is a block diagram illustrating a 3D scanner in the food taste reproduction system according to the embodiment.

In the taste recognition device 2, the voltage detection circuit 35 detects a membrane potential of the taste sensor 33 with an electric potential of the reference electrode 34 as a reference. The A/D converter circuit 36 converts the output from the voltage detection circuit 35 into a digital value. The arithmetic processing circuit 37 performs a processing such as an operation of the output from the A/D converter circuit 36. The taste data as the output from the arithmetic processing circuit 37 is transmitted to the first terminal 5 (see FIG. 1).
<3D Scanner>
FIG. 4 is a block diagram illustrating the 3D scanner in the food taste reproduction system according to the embodiment. As illustrated in FIG. 4, the 3D scanner 3 includes a laser light source 41 that irradiates the whole of a food 42 with a laser, a filter 43 that perform the color separation of the laser reflected on a surface of the food 42 into the RGB, an image sensor 44 that senses the respective colors of the RGB and outputs as an electrical signal, an A/D converter circuit 45 that performs an A/D conversion of the electrical signal output from the image sensor 44 into a digital value, and an image processing circuit 46 that performs an image processing on the output from the A/D converter circuit 45 to output as shape data and color data.

<Texture Measurement Device>

Figure 5:
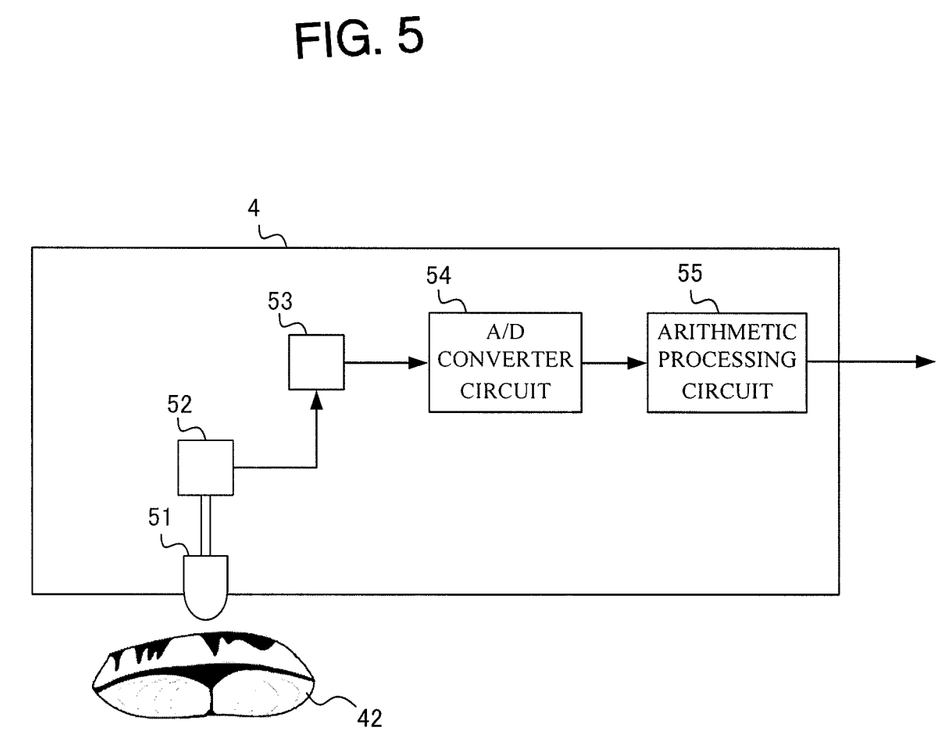
FIG. 5 is a block diagram illustrating a texture measurement device in the food taste reproduction system according to the embodiment.

FIG. 5 is a block diagram illustrating the texture measurement device in the food taste reproduction system according to the embodiment. The texture measurement device 4 includes a probe 51 pressed onto the food 42, an actuator 52 that drives the probe 51, a pressure sensor 53 that detects a stress when the probe 51 is pressed onto the food 42 and outputs it as an electrical signal, an A/D converter circuit 54 that performs an A/D conversion of the electrical signal output from the pressure sensor 53 into a digital value, and an arithmetic processing circuit 55 that performs a processing such as an operation of the output from the A/D converter circuit 45 and outputs it as the texture data.

<First Terminal>

The computer 100 (see FIG. 2) constituting the first terminal 5 as an exemplary second computer according to the embodiment may include a computer mouse and a keyboard (not illustrated) for accepting operations by an operator and a display (not illustrated) for indicating the taste data and the like as necessary. A user interface for accepting the operations by the operator is not limited to a mouse mask and the keyboard, may be, for example, an electrostatic touchscreen or a pressure sensitive touchscreen, and is not specifically limited. The display may be a touch panel display and double as the user interface and a display unit.

In the computer 100 constituting the first terminal 5, the central control unit 101 controls the serial interface 103, and receives the taste data, the shape data, the color data, and the texture data from the taste recognition device 2, the 3D scanner 3, and the texture measurement device 4.

The central control unit 101 is configured to store the information on the taste components used by the taste reproduction device 9 in the storage device 104.

The central control unit 101 is configured to execute the process to convert the taste data into the taste reproduction data on the component ratio of the taste components for reproducing the food taste by combining a plurality of the taste components used by the taste reproduction device 9.

First, the storage device 104 in the computer 100 constituting the first terminal 5 stores the information on the taste components used by the taste reproduction device 9.

The information on the taste components includes, for example, information for identifying the taste components, types of the basic tastes provided by the taste components, and strengths of these basic tastes. The information for identifying the taste components is, for example, names of the taste components or identification information (hereinafter referred to as a cartridge ID) of cartridges (described below), which house the taste components, of the taste reproduction device 9, while being not specifically limited.

Exemplary information on the taste components is a taste component table as indicated in the following Table 1. In this example, one taste component provides one basic taste, while one taste component provides a plurality of the basic tastes in some cases. In this case, the types and the strengths of the plurality of the basic tastes are associated with one cartridge ID.

TABLE 1

| CARTRIDGE ID | BASIC TASTE | STRENGTH |
|---|---|---|
| NO. 1 | BITTERNESS | 3 |
| . | . | . |
| . | . | . |
| . | . | . |
| NO. 14 | SWEETNESS | 3 |
| . | . | . |
| . | . | . |
| . | . | . |
| NO. 23 | ACIDITY | 3 |
| . | . | . |
| . | . | . |
| . | . | . |
| NO. 32 | SALTINESS | 3 |
| . | . | . |
| . | . | . |
| . | . | . |
| NO. 62 | UMAMI TASTE | 3 |
| . | . | . |
| . | . | . |
| . | . | . |
| NO. 67 | ASTRINGENCY | 3 |
| . | . | . |
| . | . | . |
| . | . | . |
| NO. 89 | PUNGENCY | 3 |
| . | . | . |
| . | . | . |
| . | . | . |
| NO. 98 | UMAMI TASTE | 3 |
| . | . | . |
| . | . | . |
| . | . | . |

The central control unit 101 constituting the first terminal 5 refers to the taste component table indicated as Table 1 based on the taste data, and selects the taste component and decides its amount to generate the taste reproduction data so as to provide a taste identical or similar to the food taste.

The central control unit 101 is configured such that the central control unit 101 adds the information on the food input by the operator via the computer mouse or the keyboard to the taste reproduction data, the shape data, the color data, and the texture data to prepare the output data, and controls the network interface 102 so as to transmit the data to the server 7 via the Internet 6. Here, the information on the food is, for example, a food name.

<Internet>

The Internet 6 includes a local area network such as LAN or WiFi, a mobile communication network, and an internet backbone network, while being not specifically limited.

<Server>

In the computer 100 (see FIG. 2) constituting the server 7 as an exemplary first computer according to the embodiment, the central control unit 101 is configured to receive the output data from the first terminal 5 and store it in the storage device 104.

Furthermore, the central control unit 101 constituting the server 7 is configured to control the network interface 102, receive a request including the information on the food from the second terminal 8 via the Internet 6, read the output data corresponding to the information on the food included in the request from the storage device 104, and control the network interface 102 to transmit the output data to the second terminal 8 via the Internet 6.

<Second Terminal>

The computer 100 (see FIG. 2) constituting the second terminal 8 as an exemplary third computer according to the embodiment may include a computer mouse and a keyboard (not illustrated) for accepting the operations by the operator and a display (not illustrated) for indicating the taste data and the like as necessary. A user interface for accepting the operations by the operator is not limited to a mouse and the keyboard, may be, for example, an electrostatic touchscreen or a pressure sensitive touchscreen, and is not specifically limited. The display may be a touch panel display and double as the user interface and a display unit. The second terminal 8 is, more specifically, a personal computer, a smart phone, a tablet, and similar device, while being not specifically limited.

The central control unit 101 constituting the second terminal 8 is configured to transmit the request of the output data including the information on the food to the server 7. The central control unit 101 is configured to control the network interface 102 so as to receive the output data from the server 7 via the Internet 6 and store it in the storage device 104 or the memory 105.

Furthermore, the central control unit 101 constituting the second terminal 8 is configured to transmit the output data stored in the storage device 104 or the memory 105 to the taste reproduction device 9 via the serial interface 103.

<Taste Reproduction Device>

Figure 6:
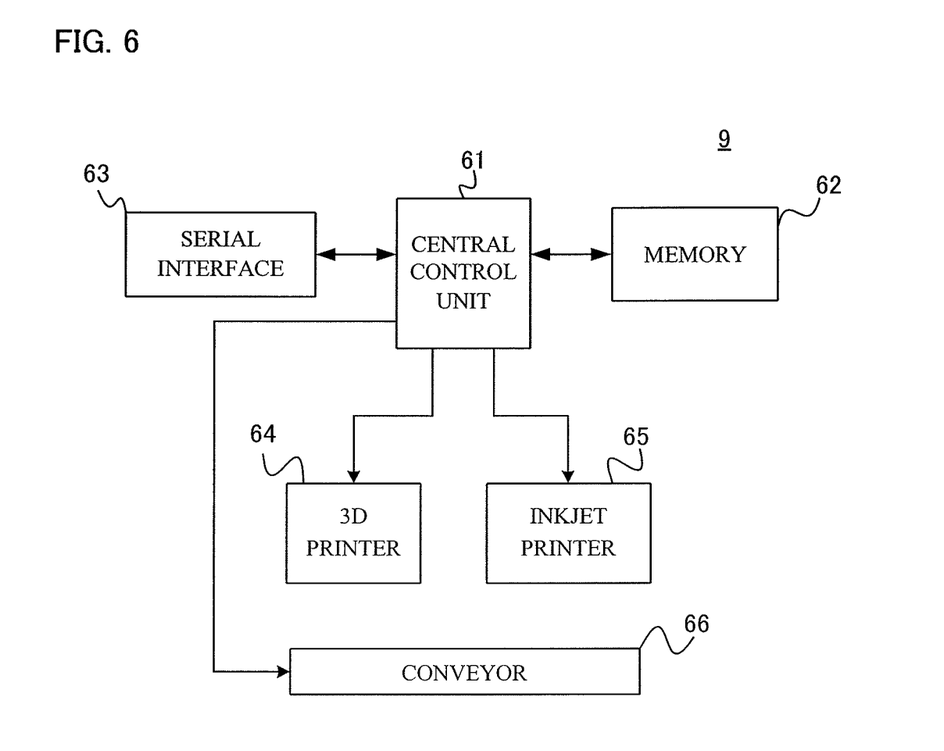
FIG. 6 is a block diagram illustrating a taste reproduction device according to the embodiment.

FIG. 6 is block diagram illustrating the taste reproduction device according to the embodiment. The taste reproduction device 9 includes a central control unit 61, a memory 62, a serial interface 63, a 3D printer 64, an inkjet printer 65, and a conveyor 66.

The central control unit 61, the memory 62, and the serial interface 63 are similar to the computer 100 described with reference to FIG. 2, thus explanations will be omitted.

The 3D printer 64 is configured to create a model including the taste components based on the taste reproduction data and the shape data in accordance with a control signal from the central control unit 61. The inkjet printer 65 is configured to color the model based on the color data in accordance with the control signal from the central control unit 61.

The conveyor 66 as a conveying unit is configured to convey the model created with the 3D printer 64 to the inkjet printer 65 in accordance with the control signal from the central control unit 61. The conveyor 66 is, for example, a belt conveyor and a robot arm, while being not specifically limited.

Figure 7:
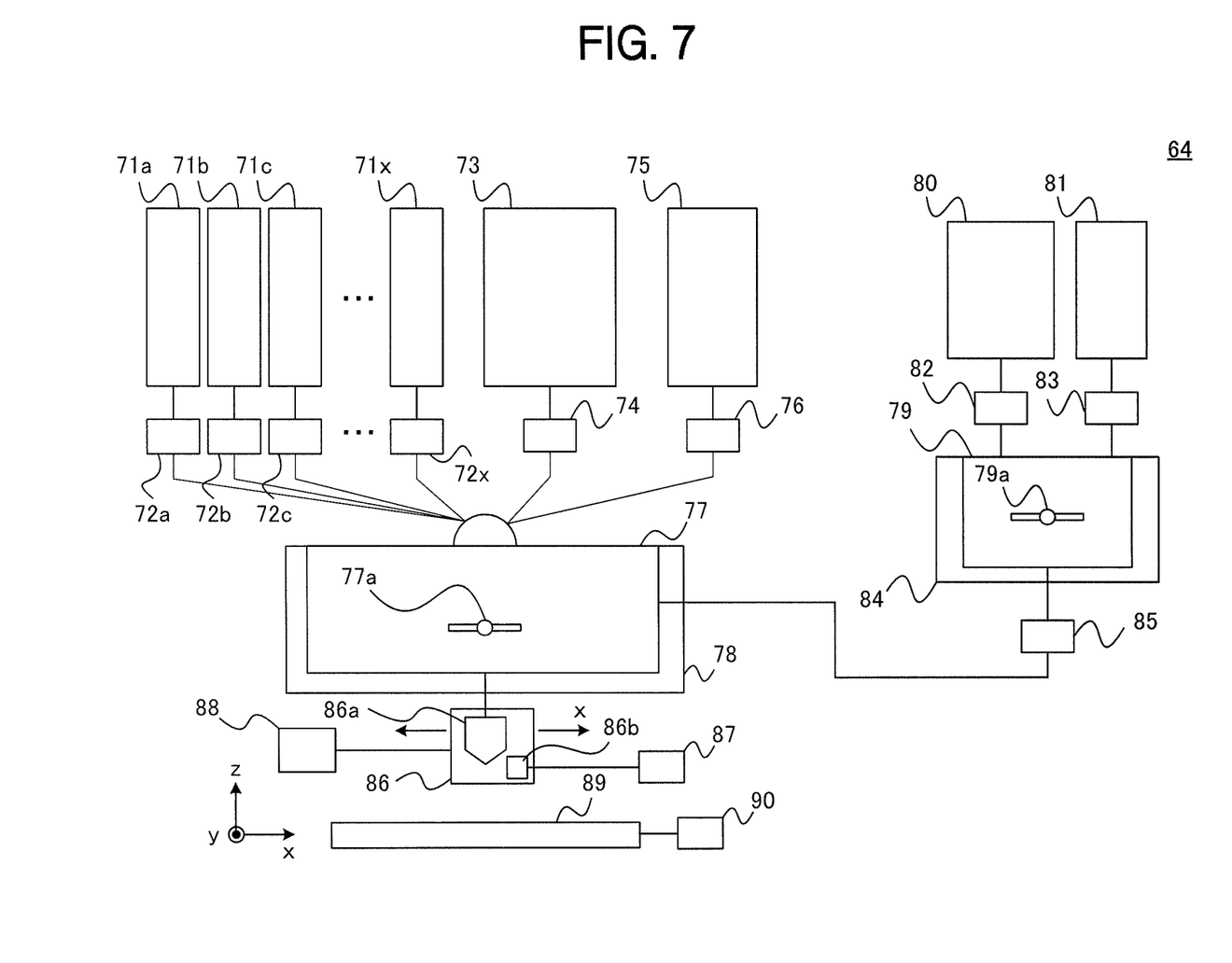
FIG. 7 is a schematic diagram illustrating a 3D printer in the taste reproduction device according to the embodiment.

Next, the 3D printer 64 will be described in more detail. FIG. 7 is a schematic diagram illustrating the 3D printer in the taste reproduction device according to the embodiment. Each unit of the 3D printer 64 is electrically coupled to the central control unit 61 and configured to operate in accordance with the control signal input from the central control unit 61, while a coupling cable and the like are not illustrated for convenience.

First, the 3D printer 64 includes a plurality of cartridges 71a to 71x as examples of storage containers. The respective cartridges 71a to 71x house different taste components. The number of the cartridges 71a to 71x is only necessary to be at least two, and not specifically limited.

On output sides of the cartridges 71a to 71x, dispensers 72a to 72x are disposed, respectively. The dispensers 72a to 72x discharge the taste components housed in the cartridges 71a to 71x at any amounts.

The 3D printer 64 also includes a tank 73 that houses water. The tank 73 includes a dispenser 74.

The 3D printer 64 also includes a tank 75 that houses a gelatinizing agent. The tank 75 includes a dispenser 76.

A first stirring tank 77 is disposed to output destinations of a plurality of the dispensers 72a to 72x, 74, and 76. The first stirring tank 77 internally includes a mixer 77a that mixes and stirs the housed materials. The first stirring tank 77 is immersed in a hot-water tank 78 with a heater, and the hot-water tank 78 is configured to warm the first stirring tank 77 at, for example, 80° C.

The 3D printer 64 includes a second stirring tank 79. To the second stirring tank 79, a tank 80 housing water and a tank 81 housing a coagulant are coupled. Dispensers 82 and 83 are disposed to output sides of the tanks 80 and 81, respectively.

The second stirring tank 79 internally includes a mixer 79a. The second stirring tank 79 is immersed in a hot-water tank 84 with a heater, and the hot-water tank 84 is configured to warm the second stirring tank 79 at, for example, 80° C.

Furthermore, a dispenser 85 is disposed to an output side of the second stirring tank 79, and its output destination is coupled to the first stirring tank 77.

A printer head 86 is coupled to the first stirring tank 77. The printer head 86 includes a print nozzle 86a and a blast nozzle 86b. Into the print nozzle 86a, a gel (a mixture C described below) as the housed material in the first stirring tank 77 is gradually flowed out. Meanwhile, a cooling gas source 87 is coupled to the blast nozzle 86b, and is configured to blow out a cooling gas to cool and coagulate the gel flowed out from the print nozzle 86a.

The printer head 86 is mounted to an actuator 88 as an exemplary driving device so as to be movable along an x-axis direction when a right-left direction with respect to a paper surface is defined as the x-axis, a vertical direction with respect to the paper surface is defined as a y-axis, and an up-down direction with respect to the paper surface is defined as a z-axis.

A stage 89 is disposed below the printer head 86. The stage 89 is mounted to an actuator 90 as an exemplary driving device so as to be movable in y-axis and z-axis directions.

Meanwhile, the inkjet printer 65 is not specifically limited insofar as a printer compatible with a general 3D printing. The inkjet printer 65 includes, for example, ink cartridges that house edible inks corresponding to cyan, magenta, yellow, and black, a printer head, a printer head control unit that drivingly controls the printer head, a movable stage on which the model is placed, and a stage drive unit that drivingly controls the stage.

<Taste Reproduction Method>

Figure 8:
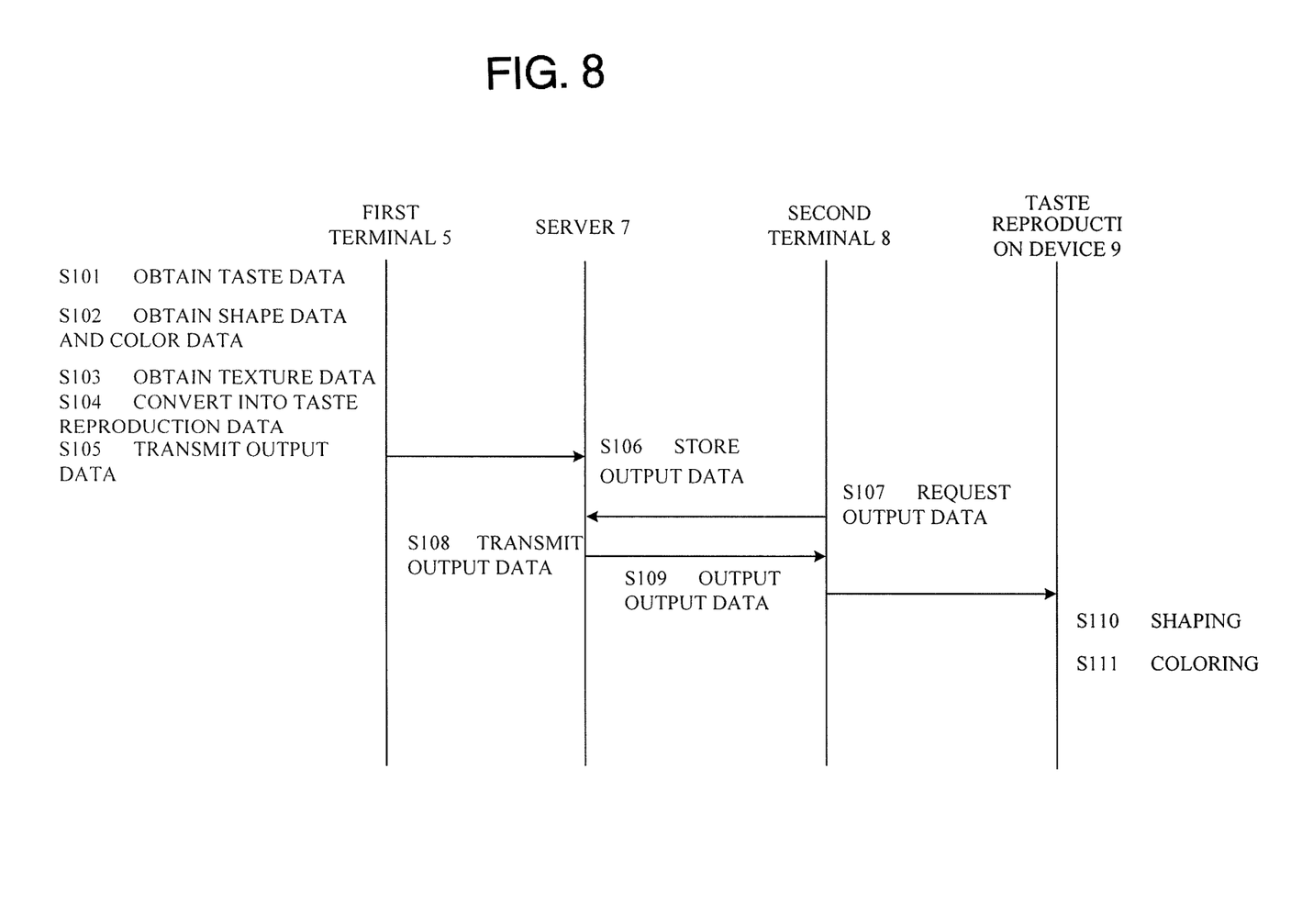
FIG. 8 is a sequence diagram illustrating each process in a food taste reproduction method according to the embodiment.

A description will be given of a food taste reproduction method according to the embodiment that uses the food taste reproduction system 1 having the above-described configuration. FIG. 8 is a sequence diagram illustrating each process in the food taste reproduction method according to the embodiment.

The food taste reproduction method mainly includes three steps of obtaining the taste data converting into the taste reproduction data, and reproducing the taste.

(a) Obtaining Taste Data

As illustrated in FIG. 8, first, the taste data is obtained (S101). The obtaining of the taste data is performed using the taste recognition device 2 (see FIG. 3). First, the solution to be measured 32 obtained by dissolving a part of the original food is put into the container 31 of the taste recognition device 2. Next, the voltage detection circuit 35 detects the membrane potential of the taste sensor 33 with the electric potential of the reference electrode 34 as a reference. Next, the A/D converter circuit 36 converts the output from the voltage detection circuit 35 into the digital value. Then, the arithmetic processing circuit 37 performs the processing such as an operation of the output from the A/D converter circuit 36, and transmits the taste data as the result to the first terminal 5 (see FIG. 1).

An example of the taste data is as indicated on the left side in Table 2 below.

TABLE 2

| TASTE DATA | | TASTE REPRODUCTION DATA | |
|---|---|---|---|
| CARTRIDGE ID | STRENGTH RATIO (%) | CARTRIDGE ID | QUANTITY (g/100 g) |
| SALTINESS | 20 | → NO. 32 | 20 |
| SWEETNESS | 20 | → NO. 14 | 20 |
| ASTRINGENCY | 5 | → NO. 67 | 5 |
| ACIDITY | 15 | → NO. 23 | 15 |
| UMAMI TASTE A | 30 | → NO. 62 | 30 |
| UMAMI TASTE B | 10 | → NO. 98 | 10 |
| PUNGENCY | 0.3 | → NO. 89 | 0.3 |

Accompanied with the obtaining of the taste data, the 3D scanner 3 (see FIG. 4) is used to obtain the shape data and the color data of the food (S102). Similarly, the texture measurement device 4 (see FIG. 5) is used to obtain the texture data of the food (S103).

(b) Converting into Taste Reproduction Data

The computer 100 (see FIG. 2) constituting the first terminal 5 converts the taste data into the taste reproduction data on the component ratio of the taste components for reproducing the food taste by combining a plurality of the taste components used by the taste reproduction device 9 (S104).

An example of the taste reproduction data is as indicated on the right side in Table 2.

Based on the texture data, a quantity a of the gelatinizing agent relative to water, a quantity b of the coagulant relative to water, and a quantity c of a mixture B (described below) mixed with a mixture A (described below). In the mixture B, the coagulant is mixed with water. In the mixture A, the taste component, the gelatinizing agent, and water are mixed. The determined quantities a, b, and c are referred to as texture reproduction data.

Next, the computer 100 (see FIG. 2) constituting the first terminal 5 (see FIG. 1) adds the information on the food input by the operator to the taste reproduction data, the shape data the color data and the texture data to prepare as the output data and transmits it to the server 7 via the Internet 6 (S105).

Next, the computer 100 (see FIG. 2) constituting the server 7 stores the output data in the storage device 104 (S106).

(c) Reproduction of Food
(c-1) Preparation

The central control unit 101 (see FIG. 2) constituting the second terminal 8 (see FIG. 1) controls the network interface 102 based on the operation performed by the operator via the computer mouse and the keyboard (not illustrated) and transmits a request to the server 7 for desired output data (S107). For example, the central control unit 101 obtains the information (for example, the food name) on the food in the output data stored in the server 7 from the server 7, and causes the display (not illustrated) to indicate it as a list. Next, the central control unit 101 accepts a selection of one piece of the information on the food performed by the operator using the computer mouse and the keyboard. Next, the central control unit 101 controls the network interface 102 to transmit the request including the selected information on the food to the server 7 via the Internet 6.

The server 7 reads the output data corresponding to the information on the food included in the request from the storage device 104 (see FIG. 2), and transmits it to the second terminal 8 (S108).

Next, the second terminal 8 controls the serial interface 103 to output the output data received from the server 7 to the taste reproduction device 9 (S109).

(c-2) Shaping

Next, the taste reproduction device 9 uses received output data to perform reproduction of the food. First, the taste reproduction data and the texture reproduction data in the output data are used to perform a shaping process (S110).

First, the 3D printer 64 causes the dispenser 74 to discharge the water from the tank 73, and supplies it to the first stirring tank 77. Next, the dispenser 76 discharges the gelatinizing agent from the tank 75 according to the quantity a included in the taste reproduction data, and supplies it to the first stirring tank 77 to be dispersed in the water. Next, the 3D printer 64 causes the dispensers 72a to 72x to discharge the taste components from the cartridges 71a to 71x according to the taste reproduction data, and supplies them to the first stirring tank 77 to be dissolved or dispersed in the water where the gel is dispersed, thus obtaining the mixture A. The mixture A is warmed to, for example, 80° C., which is higher than a solidification temperature of an agar, in the hot-water tank 78, and slowly stirred with the mixer 77a so as not to be solidified, thus the taste is uniformed.

The 3D printer 64 causes the dispensers 82 and 83 to discharge the water and the coagulant from the tanks 80 and 81 according to the quantity b included in the texture reproduction data, and supplies them to the second stirring tank 79 to be mixed with the mixer 79a, thus obtaining the mixture B. The mixture B is warmed to, for example, 80° C. in the hot-water tank 84.

Furthermore, the 3D printer 64 uses the dispenser 85 to discharge the mixture B from the second stirring tank 79 according to the quantity c included in the texture reproduction data and supplies it to the first stirring tank 77 while mixing the mixture A with the mixer 77a in the first stirring tank 77, thus mixing the mixture B with the mixture A to obtain the mixture C.

Next, the 3D printer 64 uses the mixture C to perform the shaping. The 3D printer 64 moves the printer head 86 and the stage 89 based on the shape data while outputting the mixture C from the print nozzle 86a of the printer head 86, thus forming the shape. Since the mixture C is in a soft gel state at an output moment, a cooling gas is applied to the mixture C from the blast nozzle 86b to instantaneously solidify the mixture C. Thus, the model is obtained.

Next, the conveyor 66 (see FIG. 6) carries out the model from the 3D printer 64 and conveys the model to the inkjet printer 65.

(c-3) Coloring

As illustrated in FIG. 7, when the shaping (S110) terminates, the inkjet printer 65 colors the model according to the color data (S111). In the inkjet printer 65, for example, while the printer head control unit and the stage drive unit move the printer head and the stage, respectively, the edible inks are sprayed to the model from the printer head, thus performing the coloring. Consequently, the taste reproduced material reproducing the taste, the texture, and the color of the original food is obtained.

<Effects>

As described above, the food taste reproduction system according to the embodiment converts the taste data of the original food into the taste reproduction data in the server 7. The taste reproduction device 9 is configured to reproduce the taste of the original food such that the 3D printer 64 selects at least two cartridges among the plurality of the cartridges 71a to 71x based on the types of the taste components included in the taste reproduction data and supplies the taste components to the first stirring tank 77 with the dispensers 72a to 72x according to the component ratio (in embodiment, the quantity (g) per 100 g of the food) included in the taste reproduction data, and combines the plurality of the taste components.

The 3D printer 64 is configured to use the gelatinizing agent and the coagulant as the food base material for the taste component, and adjust the hardness and the elasticity of a taste reproduced material based on the quantity a of the gelatinizing agent relative to water, the quantity b of the coagulant relative to water, and the quantity c of the mixture B relative to the mixture A, which are included in the texture reproduction data, so as to add the texture of the food to the taste reproduced material.

Furthermore, the 3D printer 64 is configured to shape the mixture C, in which the taste component, the gelatinizing agent, the coagulant and the water are mixed, according to the shape data so as to reproduce the shape of the original food.

In the taste reproduction device 9, the inkjet printer 65 is configured to color the model according to the color data so as to reproduce the color of the original food.

With the food taste reproduction system 1 according to the embodiment, the taste reproduced material can be fabricated using the taste reproduction device 9 anytime and anywhere insofar as connectable to the Internet 6, thus, for example, the foods around the world can be served beyond time and space.

The present invention is not limited to the above-described embodiment, and can be variously changed to embody. In the above-described embodiment, the components illustrated in the attached drawings are not limited to those, and may be appropriately changed in a range that can provide the effects of the present invention. Moreover, the present invention may be appropriately changed to embody without departing from a scope of the object of the present invention.

While the above-described embodiment reproduces the shape, the color, and the texture in addition to the taste of the original food, furthermore, the smell of the food may be reproduced. In this case, first, when the taste data of the original food is obtained, a smell recognition device including a smell sensor obtains smell data of the food and adds it to the output data. The server 7 converts the smell data into smell reproduction data including a type of a flavor and a combination percentage. Meanwhile, the 3D printer 64 of the taste reproduction device 9 includes a cartridge that houses the flavor in addition to the cartridges 71a to 71x that house the taste components. Then, the taste reproduction device 9 uses the smell reproduction data with the taste reproduction data, and causes the 3D printer 64 to supply the flavor from the cartridge by a predetermined amount based on the type of the flavor and the combination percentage, thus adding it to the mixture C. Consequently, the smell of the food is added to a feed taste reproduction material.

While the above-described embodiment separately includes the second terminal 8 and the taste reproduction device 9, both may be configured as one unit.

While the above-described embodiment stores the output data including the taste reproduction data in the server 7, transmits it to the second terminal 8 via the Internet 6, and inputs it to the taste reproduction device 9 from the second terminal 8, a route for inputting the output data to the taste reproduction device 9 is not limited to this. For example, the output data is downloaded to a communication terminal such as a smart phone and a tablet from the server 7 and stored in a local storage device. The user may transfer the output data from the communication terminal to the taste reproduction device 9 via a short range communication such as Bluetooth.

The output data may be stored in a memory card as an exemplary recording medium, and the output data may be read from the memory card with a memory card reader coupled to the second terminal 8 to be used. In this case, the output data can be stored in the recording medium to be distributed.

While the above-described embodiment has described the case of reproducing a solid food in an identical taste and an identical shape, the solid food may be reproduced in different shape and property while having the identical taste. For example, a solid food may be reproduced as a liquid beverage that provides an identical taste. A liquid beverage may be reproduced as a solid food or a tablet that provides an identical taste. Furthermore, the taste of the taste reproduced material may be different from a taste ordinarily imagined from its shape and color. For example, a taste reproduced material having a shape of a salt-grilled fish while having a taste of a sautéed chicken can be considered. Alternatively, a taste reproduced material may have a color different from an ordinary color while having ordinary shape and taste. For example, a taste reproduced material having a blue color and a taste of a tomato ketchup can be considered. Alternatively, a taste reproduced material may have a texture different from an appearance.

While the above-described embodiment has described the case of reproducing the taste of the food for human, the present invention is applicable to reproduction of tastes of animals other than human.

<Application>

As described above, with the food taste reproduction system according to the embodiment, the taste reproduction device 9 can easily fabricate the taste reproduced material anytime and any where using the output data including, for example, the food taste data. This ensures the following applications.

(1) Application to Nutritious Food

In the taste reproduction device 9, the taste components containing nutrients such as iron, calcium, and vitamin are prepared in addition to the materials providing the basic tastes. Meanwhile, types and amounts of nutrients to be ingested are determined in a hospital, a nursing home, and the like according to symptoms and physical conditions of a patient and a person in need of nursing care, and they are transmitted to the server 7 as nutrition data. The server 7 selects the taste component containing a desired nutrient based on the taste data, and generates the taste reproduction data. According to this taste reproduction data, the taste reproduction device 9 fabricates the taste reproduced material. The obtained taste reproduced material can provide the taste of the original food and contain the nutrient different from that of the original food. In view of this, the patient and the person in need of nursing care eating the taste reproduced material can ingest the necessary nutrient while tasting the taste of the original food.

(2) Application to Space Food

As described in (1), the use of a material containing the nutrient as the taste component provides a possibility of an application to a space food in the future. The taste reproduction device is installed in a space station and the like, and the taste reproduction data is transmitted from a base on the ground to fabricate a taste reproduction material with the taste reproduction device. This allows a person staying in space to eat a dish of a restaurant on the ground that he/she wants to eat and his/her mother's dish any time in space. Additionally, physical condition data is managed on the ground corresponding to a physical condition of an astronaut, and the taste reproduction data is generated and the taste reproduction material is fabricated with a sense reproduction device so as to include the nutrients necessary on the day, thus ensuring a control on the physical condition to the best in an extreme condition.

(3) Application to Emergency Food and Survival Food

Saving foodstuffs is indispensable to Japan as a country with many natural disasters. Developing a long-storable cartridge and installing it to, for example, schools, municipalities, and Self-Defense Force ensure quickly providing a food with high nutrient at the time of disaster. Such food can be provided with a changed distribution of nutrients corresponding to the health condition.

(4) Application to Nutrition Support Infrastructure in Poor Country

There are still many countries where food does not grow due to a climate or an environment or countries suffered from hunger. Developing the technique according to the embodiment ensures transferring the taste and the nutrient to carry beyond the space. A delicious food with high nutrients can be provided to many people around the world. Furthermore, the physical condition is remotely measured without presence of a doctor and a nutritionist, thus a nutrition-balanced food can be provided.

(5) Application to Athlete Food

The food taste reproduction system is adaptable to a food menu of a top athlete that requires a body in the extreme condition. A body condition is measured in real-time, and a menu with a nutrient balance adjusted to that occasion is automatically transmitted, thus ensuring outputting the menu for eating. A material (for example, a liquid, a jelly, and a tablet) in consideration of a speed of ingestion into the body is also selectable.

(6) Application to Handing Down and Conservation of Food

Converting the taste data of the food into detailed data and preparing a large amount of output side cartridges ensures reproducing detailed tastes. A traditional food unique to Japan, a taste of a cook reproducible by only one person in the world, a homemade dish by mother, and similar taste can be reproduced in detail, and the food taste reproduction system is applicable to not only "transfer" of the food but also the handing down and the conservation of the food.

(7) Application to Study and Development of Cooking

Laboratories and cooks scattered around the world are connected to share the taste of the food, thus ensuring product development of a new food beyond space. Producing a new food is ensured while gathering wisdom around the world beyond time and space.

The terms described in this Description and/or the terms necessary for understanding this Description may be replaced to terms having identical or similar meanings.

The information, the signal, and the like described in this Description may be indicated using any of various different techniques. For example, the data, the instruction, the command, the information, the signal, the bit, the symbol, and the chip, which can be mentioned through the above-described entire explanation, may be indicated by a voltage, a current, an electromagnetic wave, a magnetic field or a magnetic particle, an optical field or a photon, or any combination of them.

The respective aspects/embodiments described in this Description may be used alone, may be used in combination, or may be switchingly used in accordance with execution. The notification of predetermined information (for example, the notification of "being X") may be implicitly (for example, by not performing the notification of this predetermined information) performed not limiting to the notification explicitly performed.

The order of the procedure, the sequence, the flowchart, and the like of the respective aspects/embodiments described in this Description may be changed insofar as it is consistent. For example, the method described in this Description presents the elements of the various steps in an exemplary order, and the method is not limited to the presented specific order.

While the present invention has been described in detail as described above, it is apparent for a person skilled in the art that the present invention is not limited to the embodiments described in this Description. The present invention can be embodied as modified and changed aspects without departing the gist and the range of the present invention determined by the disclosure in claims. Therefore, the description in this Description is made for the explanation of the examples, and has no restrictive meaning on the present invention.

INDUSTRIAL APPLICABILITY

The present invention provides an effect that a taste reproduced material reproducing a taste of an original food can be obtained anytime and anywhere, and is appropriately usable for, especially, provision of a food, a medical treatment, a nursing care, provision of an emergency food and a nutritious food, studies on food and cooking, for example.

This application is based on Japanese Patent Application No. 2016-53311 filed on Mar. 17, 2016, and the disclosure of which is incorporated herein.

The invention claimed is:

1. A food taste reproduction apparatus comprising:
a first computer configured to convert taste data into taste reproduction data, the taste data being obtained by quantifying a taste of a food, the taste reproduction data being data on a component ratio of taste components for reproducing the taste by combining a plurality of the taste components, the taste component containing a material providing at least one basic taste; and
a taste reproduction device configured to obtain a taste reproduced material such that the taste reproduction device selects at least two taste components among the plurality of the taste components based on the taste reproduction data and combines the selected taste components according to the component ratio.

2. The food taste reproduction apparatus according to claim 1, wherein
the taste reproduction device further includes a shaping device configured to shape the taste reproduced material into a shape of the food based on shape data on the shape of the food.

3. The food taste reproduction apparatus according to claim 2, wherein the shaping device mixes a food base material with the taste component based on texture data on a texture of the food, and adds the texture of the food to the taste reproduced material.

4. The food taste reproduction apparatus according to claim 1, wherein the taste reproduction device further includes a coloring device configured to perform coloring on the taste reproduced material based on color data of the food.

5. The food taste reproduction apparatus according to claim 1, wherein the first computer refers to eating person data on an eating person who eats the taste reproduced material to select the taste component or decide an amount of the taste component corresponding to the eating person.

6. The food taste apparatus according to claim 1, further comprising:

a taste sensor configured to output the taste as an electrical signal; and a second computer configured to output the taste data obtained by quantifying the taste based on the electrical signal output by the taste sensor.

7. The food taste reproduction apparatus according to claim 1, wherein the taste reproduction device includes a plurality of storage containers, a supply unit, and a combination unit, the plurality of the storage containers separately storing a plurality of the taste components, the supply unit supplying any amount of the taste components from at least two of the plurality of the storage containers based on the taste reproduction data, the combination unit combining the plurality of taste components supplied from the supply unit.

8. The food taste reproduction apparatus according to claim 2, wherein the first computer refers to eating person data on an eating person who eats the taste reproduced material to select the taste component or decide an amount of the taste component corresponding to the eating person.

9. The food taste reproduction apparatus according to claim 8, wherein the shaping device mixes a food base material with the taste component based on texture data on a texture of the food, and adds the texture of the food to the taste reproduced material.

10. The food taste reproduction apparatus according to claim 8, wherein the taste reproduction device further includes a coloring device configured to perform coloring on the taste reproduced material based on color data of the food.

11. The food taste reproduction apparatus according to claim 8, further comprising:

a taste sensor configured to output the taste as an electrical signal; and a second computer configured to output the taste data obtained by quantifying the taste based on the electrical signal output by the taste sensor.

12. The food taste reproduction apparatus according to claim 8, wherein the taste reproduction device includes a plurality of storage containers, a supply unit, and a combination unit, the plurality of the storage containers separately storing a plurality of the taste components, the supply unit supplying any amount of the taste components from at least two of the plurality of the storage containers based on the taste reproduction data, the combination unit combining the plurality of the taste components supplied from the supply unit.

13. A food taste reproduction method comprising:

converting taste data into taste reproduction data with a first computer, the taste data being obtained by quantifying a taste of a food, the taste reproduction data being data on a component ratio of taste components for reproducing the taste of the food by combining a plurality of the taste components, the taste component containing a material providing at least one basic taste; and obtaining a taste reproduced material such that a second computer controls a taste reproduction device that selects at least two taste components among a plurality of the taste components based on the taste reproduction data and combines the selected taste components according to the component ratio.

* * * * *